(12) United States Patent
Huang et al.

(10) Patent No.: US 12,311,138 B2
(45) Date of Patent: May 27, 2025

(54) AREA ARRAY MICRO-NEEDLE STRUCTURE

(71) Applicant: WUHAN NEURACOM TECHNOLOGY DEVELOPMENT CO., LTD., Wuhan (CN)

(72) Inventors: Li Huang, Wuhan (CN); Cheng Huang, Wuhan (CN); Bei Tong, Wuhan (CN)

(73) Assignee: WUHAN NEURACOM TECHNOLOGY DEVELOPMENT CO., LTD., Wuhan (CN)

( * ) Notice: Subject to any disclaimer, the term of this patent is extended or adjusted under 35 U.S.C. 154(b) by 0 days.

(21) Appl. No.: 18/969,639

(22) Filed: Dec. 5, 2024

(65) Prior Publication Data

US 2025/0090825 A1 Mar. 20, 2025

Related U.S. Application Data

(63) Continuation of application No. PCT/CN2022/127286, filed on Oct. 25, 2022.

(30) Foreign Application Priority Data

Aug. 24, 2022 (CN) .......................... 202211015891.9

(51) Int. Cl.
*A61M 37/00* (2006.01)
(52) U.S. Cl.
CPC . *A61M 37/0015* (2013.01); *A61M 2037/0061* (2013.01)

(58) Field of Classification Search
CPC .................. A61M 37/0015; A61M 2037/0061
(Continued)

(56) References Cited

U.S. PATENT DOCUMENTS

2010/0331935 A1* 12/2010 Tabada ..................... A61N 1/05
600/377
2016/0339223 A1 11/2016 Scherr et al.
(Continued)

FOREIGN PATENT DOCUMENTS

CN 101919734 A 12/2010
CN 112617822 A 4/2021
(Continued)

OTHER PUBLICATIONS

International Search Report and Written Opinion issued in corresponding PCT Application No. PCT/CN2022/127286, dated Feb. 22, 2023.
(Continued)

*Primary Examiner* — Phillip A Gray
(74) *Attorney, Agent, or Firm* — Westbridge IP LLC (57) ABSTRACT

Disclosed is an area array micro-needle structure, including a positioning partition plate and at least one micro-needle assembly. The positioning partition plate includes at least two comb structure members stacked to form a plurality of micro-needle holes for a body electrode of a micro-needle to pass through. The positioning partition plate can provide the positioning guiding and fixing effects when the area array micro-needles are implanted, so that accurate implantation of the micro-needles is achieved; the micro-needles can be pulled out after being completely implanted, without damaging human organs and tissues.

7 Claims, 12 Drawing Sheets

(58) Field of Classification Search
USPC .......................................................... 604/500
See application file for complete search history.

(56) References Cited

U.S. PATENT DOCUMENTS

| | | | |
|---|---|---|---|
| 2017/0340283 A1* | 11/2017 | Palaniappa | ............ A61B 5/685 |
| 2020/0331691 A1 | 10/2020 | Sakazaki et al. | |
| 2021/0204878 A1 | 7/2021 | Huang | |

FOREIGN PATENT DOCUMENTS

| | | |
|---|---|---|
| CN | 213851016 U | 8/2021 |
| CN | 113856031 A | 12/2021 |
| CN | 114209330 A | 3/2022 |
| CN | 114305433 A | 4/2022 |
| CN | 114343654 A | 4/2022 |
| CN | 114469108 A | 5/2022 |
| CN | 114469117 A | 5/2022 |
| CN | 114515152 A | 5/2022 |
| CN | 114788700 A | 7/2022 |
| JP | 2007046422 A | 2/2007 |
| JP | 2009030328 A | 2/2009 |
| JP | 2012202017 A | 10/2012 |
| KR | 20090025937 A | 3/2009 |
| KR | 20190111682 A | 10/2019 |

OTHER PUBLICATIONS

Notification to Grant Patent Right for Invention issued in counterpart Chinese Patent Application No. 202211015891.9, dated Dec. 12, 2023.

* cited by examiner

AREA ARRAY MICRO-NEEDLE STRUCTURE

CROSS-REFERENCE TO RELATED APPLICATIONS

The present application is a continuation application of International Application No. PCT/CN2022/127286, filed on Oct. 25, 2022, which claims priority to Chinese Patent Application No. 202211015891.9, filed on Aug. 24, 2022. The disclosures of the above-mentioned applications are incorporated herein by reference in their entireties.

TECHNICAL FIELD

The present application relates to the technical field of brain-computer interface neural microelectrode, and in particular to an area array micro-needle structure.

BACKGROUND

In the neural interface, brain signals are collected by electrodes, including invasive and non-invasive forms, and the brain signals collected by invasive electrodes are more accurate and reliable. However, when the existing invasive micro-needle structure is used in practice, the operation is difficult when the invasive micro-needle is set. Due to the limitations of the operation, it is impossible to accurately set the micro-needle and avoid the displacement of the target tissue.

In addition, most of the existing invasive micro-needle structures are single-type electrodes, such as Michigan electrodes and Utah electrodes with hard needle structures, and polyimide electrodes with soft needle structures. However, the hard needle (rigid needle) cannot be deformed adaptively with the expansion and contraction of the blood vessels during implantation, which may cause certain damage to the tissue; and the soft needle structure is prone to deformation during implantation and requires the assistance of external equipment for implantation, which has problems such as complex structure and low efficiency. In addition, the functions of the hard needle or the soft needle are relatively simple, that is, they only have recording function and do not have stimulation effect. More importantly, the electroencephalogram (EEG) signal has a small amplitude, a low frequency range and is easily interfered by noise, and the extraction of the EEG signals in the related art is not accurate enough.

SUMMARY

The purpose of the present application is to provide an area array micro-needle structure, which can at least solve some of the defects existing in the related art.

To achieve the above purpose, the present application adopts the following technical solutions:

A positioning partition plate, including: at least two comb structure members stacked to form a plurality of micro-needle holes for a body electrode of a micro-needle to pass through.

In an embodiment, the comb structure member includes a connecting plate and a plurality of racks formed on the connecting plate, and each of the racks is connected to the connecting plate in parallel at equal intervals; and the racks of the comb structure members are stacked to form the plurality of micro-needle holes distributed in an array.

In an embodiment, a spacing between the racks of the comb structure members is slightly larger than a width of the body electrode of the micro-needle or a thickness of the body electrode of the micro-needle.

In addition, the present application also provides an area array micro-needle structure, including: the positioning partition plate and at least one micro-needle assembly; the micro-needle assembly includes a micro-needle body, an integrated circuit chip provided at a tail of the micro-needle body, and a microstrip wire fixedly connected to one end of the integrated circuit chip to form an electrical connection; and the body electrode of each micro-needle body is configured to pass through the micro-needle hole of the positioning partition plate.

In an embodiment, the micro-needle body includes a hard needle and a soft needle; the hard needle is provided with a hard needle tail and at least one hard needle body electrode formed on the hard needle tail, and the soft needle is provided with a soft needle tail and at least one soft needle body electrode formed on the soft needle tail; and the soft needle body electrode is correspondingly fixed with the hard needle body electrode through a first fixing member, and the soft needle tail is fixed with the hard needle tail through a second fixing member; the integrated circuit chip is electrically connected to the soft needle tail through reverse welding.

In an embodiment, the first fixing member is a plurality of hook structures provided at intervals along a length direction of the hard needle body electrode, and the hook structure is provided with a first part and a second part; one end of the second part is connected to the first part, and the other end of the second part is connected to a surface of the hard needle body electrode; the first part is parallel to the surface of the hard needle body electrode; and the soft needle body electrode is provided between the first part and the surface of the hard needle body electrode, and the second part is at a preset angle relative to the surface of the hard needle body electrode.

In an embodiment, an opening is provided on the soft needle body electrode at a position corresponding to the hook structure for the hook structure to pass through, and an unhook structure is provided on the opening for the hook structure to detach from the soft needle; the unhook structure is an unhook portion extending from an edge of the opening into an inside of the opening, and a spacing between unhook portions is smaller than a width of the hook structure; and the unhook portions are symmetrically provided along an axis of the opening, and a gap is provided between a side edge of the unhook portion and a corresponding side edge of the opening.

In an embodiment, the second fixing member is a plurality of pin structures provided at intervals along a width direction of the hard needle tail, and the pin structure includes two coaxial cylinders larger at upper part and smaller at lower part; and a pin hole is provided at the soft needle tail corresponding to the pin structure; a plurality of central symmetrical figures are provided outward along an edge of the pin hole on the soft needle tail, and a diameter of an upper cylinder of the pin structure is greater than a diameter of the pin hole.

In an embodiment, connecting through holes are provided at both ends of the integrated circuit chip; a plurality of integrated circuit chips are assembled together through a binding structure, and the binding structure is configured to pass through connecting through holes on a same side.

In an embodiment, the microstrip wire includes a bus and a plurality of branch wires connected with the bus, and each of the branch wires is correspondingly welded and fixed to one end of each of the integrated circuit chips through reverse welding.

Compared with the related art, the present application has the following beneficial effects:

(1) The positioning partition plate provided by the present application can play a role in positioning, guiding and fixing when the area array micro-needle is implanted, thereby realizing the precise implantation of the micro-needle. After the micro-needle is fully implanted, it can be pulled out without causing damage to human organs and tissues.

(2) The area array micro-needle provided by the present application can realize the real-time, rapid and accurate extraction and stimulation of neural signals by directly welding the micro-needle array to the integrated circuit chip, thereby minimizing transmission loss and reducing noise signals, so as to ensure stable and lossless signal transmission.

(3) In the area array micro-needle structure provided by the present application, the micro-needle body is designed as a composite structure of a hard needle and a soft needle. The hard needle is configured to bring the soft needle into the tissue, and the hard needle is pulled out, thereby avoiding the defects of using a single hard needle or a single soft needle.

(4) In the area array micro-needle structure provided by the present application, by patterning the unhook structure on the soft needle body electrode of the soft needle and growing the hook structure at the corresponding position of the hard needle, on the one hand, the soft needle can be driven to be implanted through the hook structure, and on the other hand, the hard needle and the soft needle can be well fixed to prevent them from moving, while reducing the risk of the soft needle warping.

(5) In the area array micro-needle structure provided by the present application, by patterning the central symmetrical figure on the soft needle tail and growing the pin structure at the corresponding position of the hard needle, the hard needle and the soft needle can be well fixed to prevent them from moving, thereby ensuring the stability and accuracy of the soft needle implantation.

The present application will be further described in detail below with reference to the accompanying drawings.

DETAILED DESCRIPTION OF THE EMBODIMENTS

The technical solutions of the embodiments of the present application will be described in more detail below with reference to the accompanying drawings. It is obvious that the embodiments to be described are only some rather than all of the embodiments of the present application. All other embodiments obtained by those skilled in the art based on the embodiments of the present application without creative efforts shall fall within the scope of the present application.

In the description of the present application, it should be understood that the terms "center", "upper", "lower", "front", "back", "left", "right", "vertical", "horizontal", "top", "bottom", "inside", "outside" indicate positions or positional relationships based on the positions or positional relationships shown in the accompanying drawings, which are only for the convenience of describing the present application and simplifying the description, rather than indicating or implying that the device or element referred to must have a specific orientation, be constructed and operated in a specific orientation, and therefore cannot be understood as a limitation of the present application.

In the description of the present application, it should be noted that, unless otherwise clearly specified and limited, the terms "installed", "connected" and "connecting" should be understood in a broad sense, for example, it can be a fixed connection, a detachable connection, an abutting connection or an integral connection. For those skilled in the art, the specific meanings of the above terms in the present application can be understood according to specific circumstances.

The descriptions of "first", "second", etc. Are only for the purpose of description, and should not be construed as indicating or implying relative importance or implicitly indicates the number of technical features indicated. Thus, a feature delimited with "first", "second" may expressly or implicitly include at least one of that feature. In the description of the present application, unless otherwise specified, "plurality of" means two or more.

First Embodiment

Figure 1:
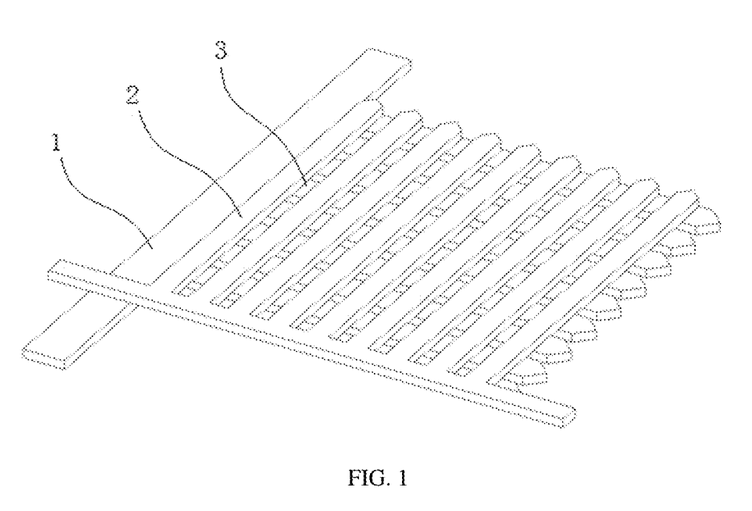
FIG. 1 is a schematic structural view of a positioning partition plate of the present application.

As shown in FIG. 1, this embodiment provides a positioning partition plate, including at least two comb structure members stacked and provided to form a plurality of micro-needle holes 3 for the body electrodes of the micro-needle to pass through. In actual use, the positioning partition plate and the micro-needle are used in combination, and the micro-needle includes at least one body electrode, which passes through the corresponding micro-needle hole 3 on the positioning partition plate to fix and position the micro-needle.

The number of the micro-needle holes 3 can be one or more, depending on the number of body electrodes contained in the micro-needle, and the distribution form of the micro-needle holes 3 can be array distribution or staggered distribution, depending on the distribution form of the body electrodes contained in the micro-needle, which is not specifically limited here.

Specifically, in this embodiment, the comb structure member includes a connecting plate 1 and a plurality of racks 2 formed on the connecting plate 1, and each of the racks 2 is connected to the connecting plate 1 in parallel at equal intervals. The racks 2 of the comb structure member are stacked on each other to form a plurality of micro-needle holes 3 distributed in an array. Furthermore, the spacing between the racks 2 of the comb structure member is slightly larger than the width of the body electrode of the micro-needle or the thickness of the body electrode of the micro-needle, so as to ensure that the body electrode of the micro-needle can move up and down between the racks without shaking, and the micro-needle is fixed and positioned in two directions of the width and thickness of the body electrode through the comb structure, so as to realize the precise implantation of the micro-needle. At the same time, after the micro-needle is completely implanted, the positioning partition plate can be easily pulled out without causing damage to human organs and tissues.

Second Embodiment

Figure 2:
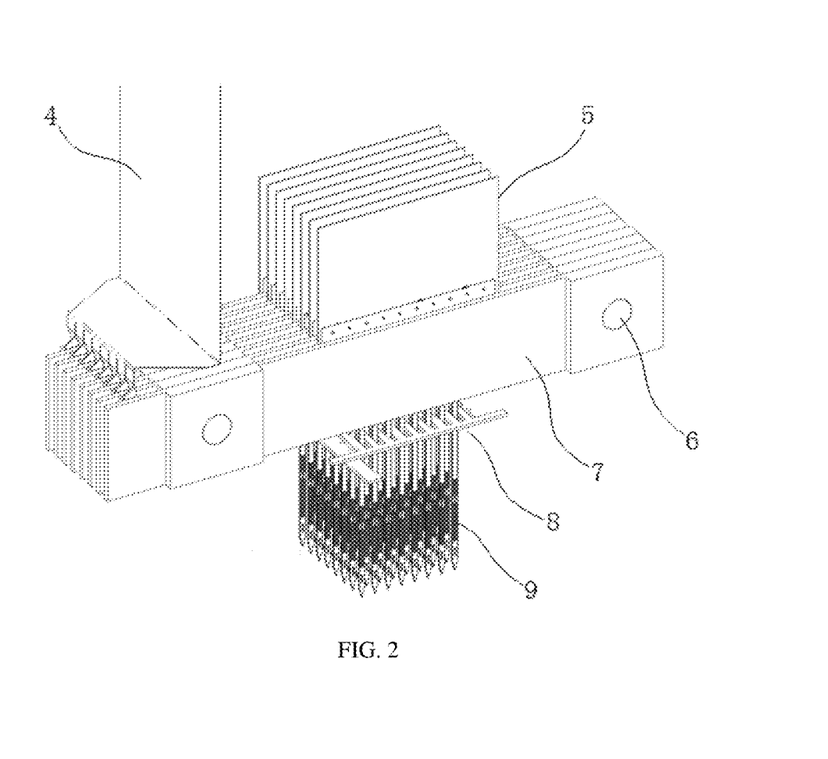
FIG. 2 is a schematic structural view of an area array micro-needle of the present application.

As shown in FIG. 2, this embodiment provides an area array micro-needle structure, including the positioning partition plate 8 and at least one micro-needle assembly. The micro-needle assembly includes a micro-needle body 5, an integrated circuit chip 7 and a microstrip wire 4. The integrated circuit chip 7 is provided at the tail of the micro-needle body 5, and the microstrip wire 4 is fixedly connected to one end of the integrated circuit chip 7 to form an electrical connection. The body electrode 9 of each micro-needle body 5 passes through the corresponding micro-needle hole 3 on the positioning partition plate 8. In this embodiment, during the implantation of the area array micro-needle structure into the tissue, and the positioning partition plate 8 is configured to guide the implantation process of each body electrode 9, thereby realizing the precise implantation of the micro-needle. The micro-needle body 5 and the integrated circuit chip 7 are integratedly designed, so as to realize the on-site acquisition and stimulation of neural signals, and accordingly optimize the functionality of the neural interface to better meet clinical needs.

Figure 3:
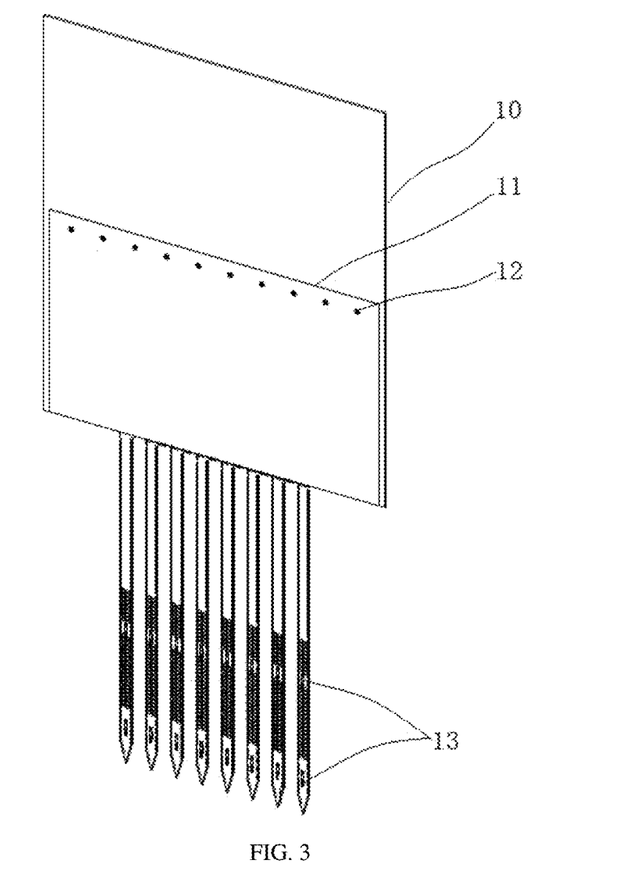
FIG. 3 is a schematic structural view of a micro-needle body of the present application.
Figure 4:
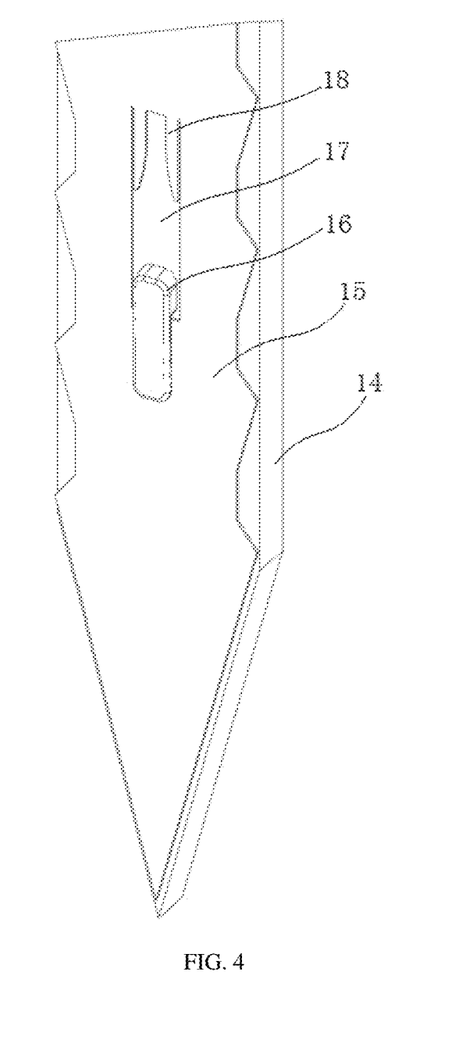
FIG. 4 is a schematic fixed structural view of a hard needle body electrode and a soft needle body electrode of the present application.
Figure 7:
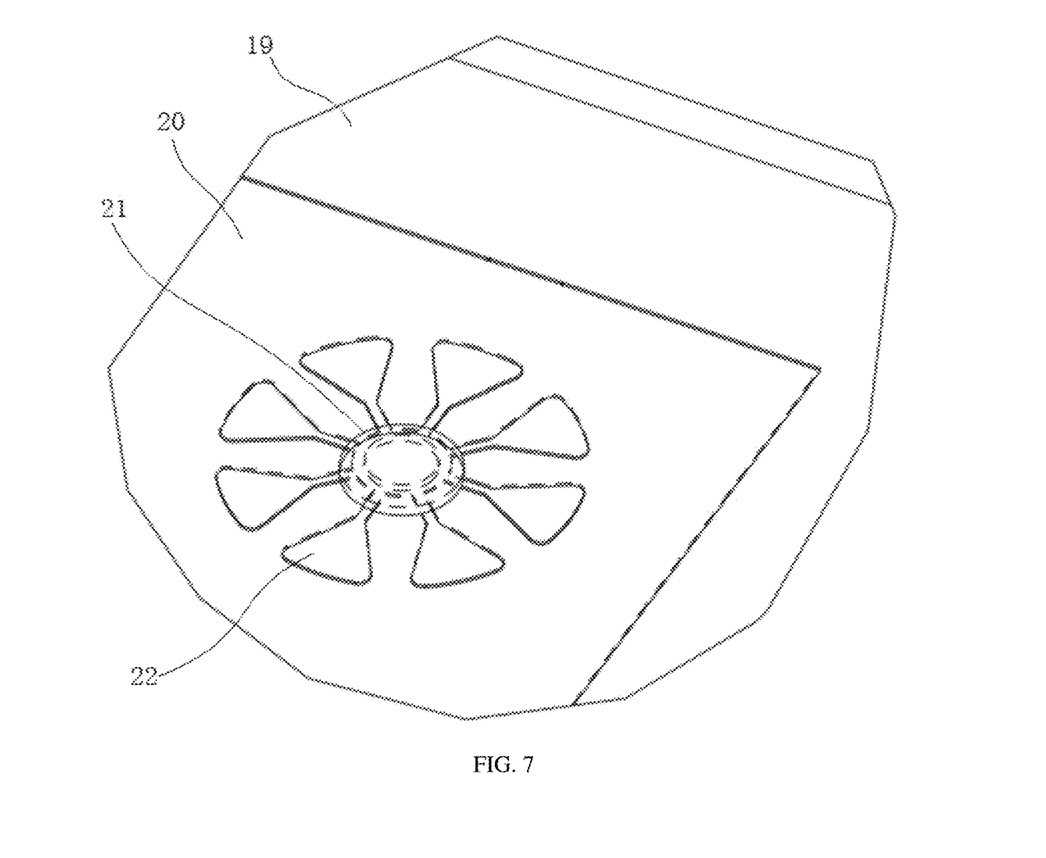
FIG. 7 is a schematic fixed structural view of a hard needle tail and a soft needle tail of the present application.
Figure 11:
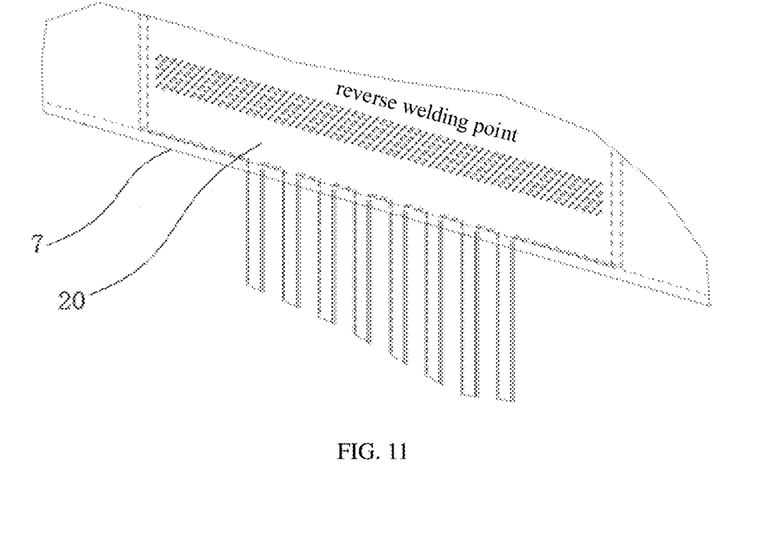
FIG. 11 is a schematic view of a reverse welding of a micro-needle body and the integrated circuit chip of the present application.

In an embodiment, as shown in FIG. 3, FIG. 4 and FIG. 7, the micro-needle body 5 includes a hard needle 10 and a soft needle 11, the hard needle 10 is provided with a hard needle tail 19 and at least one hard needle body electrode 14 formed on the hard needle tail 19, and the soft needle 11 is provided with a soft needle tail 20 and at least one soft needle body electrode 15 formed on the soft needle tail 20. The soft needle body electrode 15 and the hard needle body electrode 14 are fixed correspondingly by a first fixing member 13, and the soft needle tail 20 and the hard needle tail 19 are fixed by a second fixing member 12. As shown in FIG. 11, the integrated circuit chip 7 and the soft needle tail 20 are electrically connected by reverse welding. The hard needle 10 is of a certain rigidity, and can be implanted into the soft tissue of the human body or the animal. For example, the hard needle 10 can be made of silicon material. The soft needle 11 is of a certain flexibility, for example, the soft needle 11 can be made of silicon nitride, polycrystalline silicon, silicon carbide and other materials. In this embodiment, since the hard needle 10 is of a certain rigidity, the soft needle 11 is laid flat on the upper surface of the hard needle 10, and the hard needle 10 and the soft needle 11 are fixed by the first fixing member 13 and the second fixing member 12 at the same time, so that the hard needle 10 can drive the soft needle 11 to be implanted into the soft tissue of the human body or the animal, and it can be ensured that no displacement occurs between the hard needle 10 and the soft needle 11. After the soft needle 11 is implanted into the tissue, the hard needle 10 is pulled out, the hard needle 10 is separated from the soft needle 11, and the soft needle 11 remains in the implanted tissue, thereby effectively avoiding the defects caused by using a single hard needle or a single soft needle.

Figure 5:
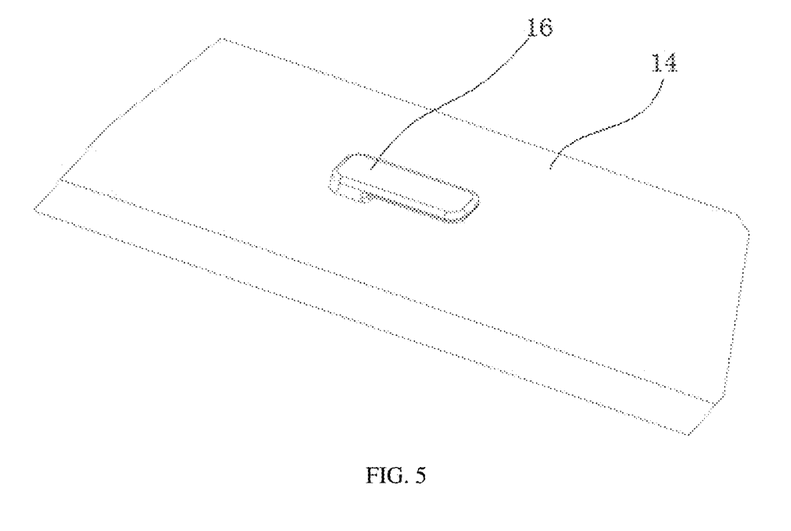
FIG. 5 is a schematic structural view of the hard needle body electrode of the present application.
Figure 6:
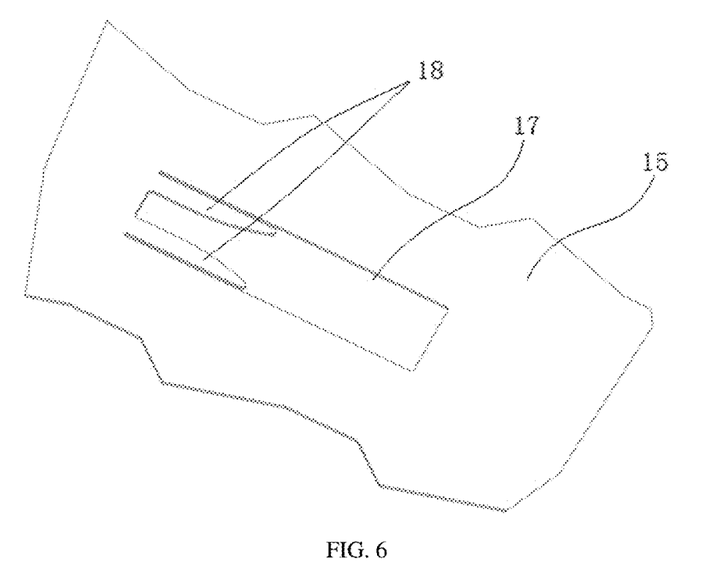
FIG. 6 is a schematic structural view of the soft needle body electrode of the present application.

In an embodiment, as shown in FIG. 4, FIG. 5 and FIG. 6, the first fixing member 13 is a plurality of hook structures 16 provided at intervals along the length direction of the hard needle body electrode 14, and the hook structure 16 has a first part and a second part. The two ends of the second part are respectively connected to the first part and the surface of the hard needle body electrode 14, the first part is parallel to the surface of the hard needle body electrode 14, the soft needle body electrode 15 is provided between the first part and the surface of the hard needle body electrode 14, and the second part is at a preset angle to the surface of the hard needle body electrode 14. Accordingly, an opening 17 for the hook structure 16 to pass through is provided at the position corresponding to the hook structure 16 on the soft needle body electrode 15, and an unhook structure for the hook structure 16 to detach from the soft needle 11 is provided on the opening 17. Specifically, the first part, the second part of the hook structure 16 and the surface of the hard needle body electrode 14 form a groove towards the needle tip of the hard needle 10, and the unhook structure is provided on the opening 17 at one end away from the needle tip of the soft needle 11. When preparing the micro-needle body composed of the hard needle 10 and the soft needle 11, a sacrificial layer of a certain thickness is first grown on the surface of the hard needle 10, and the soft needle 11 is grown on the surface of the sacrificial layer. An opening 17 is opened on the soft needle body electrode 15 of the soft needle 11, the unhook structure is patterned on the soft needle 11, and the second part of the hook structure 16 is grown at the opening 17. Finally the first part of the hook structure 16 is grown, and the sacrificial layer between the hard needle 10 and the soft needle 11 is released, so that part of the soft needle body electrode 15 at the edge of the opening 17 is pressed into the hook structure 16. When the hard needle 10 is implanted into the tissue, the soft needle 11 is implanted together through the hook structure 16. After reaching the implantation site, the hard needle 10 is pulled backward. After the hook structure 16 on the hard needle body electrode 14 contacts the unhook structure at the rear end of the opening 17, the unhook structure makes the hook structure 16 detached from the soft needle body electrode 15, and fixation between the soft needle body electrode 15 and the hard needle body electrode 14 is released, so that the hard needle 10 is pulled out while the soft needle 11 remains in the tissue.

In an embodiment, as shown in FIG. 6, the unhook structure is two unhook portions 18 extending from the edge of the opening 17 to the inside of the opening 17, and the two unhook portions 18 are symmetrically provided along the axis of the opening. There is a spacing between the two unhook portions 18, which is smaller than the width of the second part of the hook structure 16, and there is a gap between the side edges of the two unhook portions 18 and the corresponding side edges of the opening 17, so that the unhook portions 18 can be turned up and squeezed in both directions. When the hard needle 10 is pulled out, the hard needle 10 is pulled back, and after the hook structure 16 contacts the unhook portion 18, the unhook portion 18 will slowly tilt upward, so that the hook structure 16 exits the opening 17 downward. The two unhook portions 18 and the soft needle body electrode 15 can be designed as an integrally formed structure, so that when the two unhook portions 18 are opened upward, the second part of the hook structure 16 squeezes the unhook portion 18, and the unhook portion 18 is tilted upward along the retreating direction of the hard needle 10, thereby expanding the area of the opening 17. The hook structure 16 is separated from the soft needle 11 in the opening 17, and the soft needle 11 and the unhook portion 18 are elastic materials. After the hard needle 10 is separated from the soft needle 11, the tilted part of the unhook portion 18 drops and returns to its original shape.

In an embodiment, as shown in FIG. 4 to FIG. 6, in order to improve the strength of the hook structure 16, the first part and the second part of the hook structure 16 are integrally formed. In the process of separating the hard needle 10 and the soft needle 11, in order to facilitate the hook structure 16 to detach from the opening 17, and to avoid the first part from affecting the unhook portion 18 during the process of the hook structure 16 squeezing the unhook portion 18, in this embodiment, the bottom surface of the second part is designed to abut against the surface of the hard needle body electrode 14, the top surface of the second part abuts against the bottom surface of the first part, and the bottom surface of the second part is larger than the top surface of the second part.

In order to facilitate the hard needle 10 to detach from the soft needle 11, in this embodiment, the angle between the second part of the hook structure 16 and the surface of the hard needle body electrode 14 is set to an acute angle, that is, to avoid the first part from exceeding the end of the second part in the direction away from the needle tip of the hard needle 10. At the same time, it is conducive for the second part of the hook structure 16 to squeeze the unhook portion 18 and cause the unhook portion 18 to tilt upward.

Figure 8:
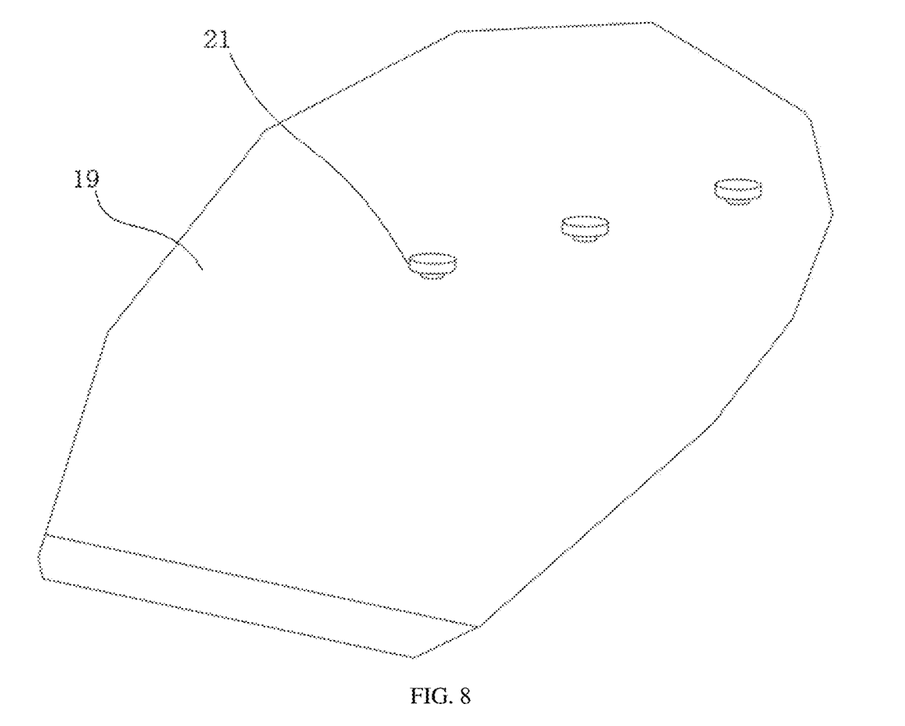
FIG. 8 is a schematic structural view of the hard needle tail of the present application.
Figure 9:
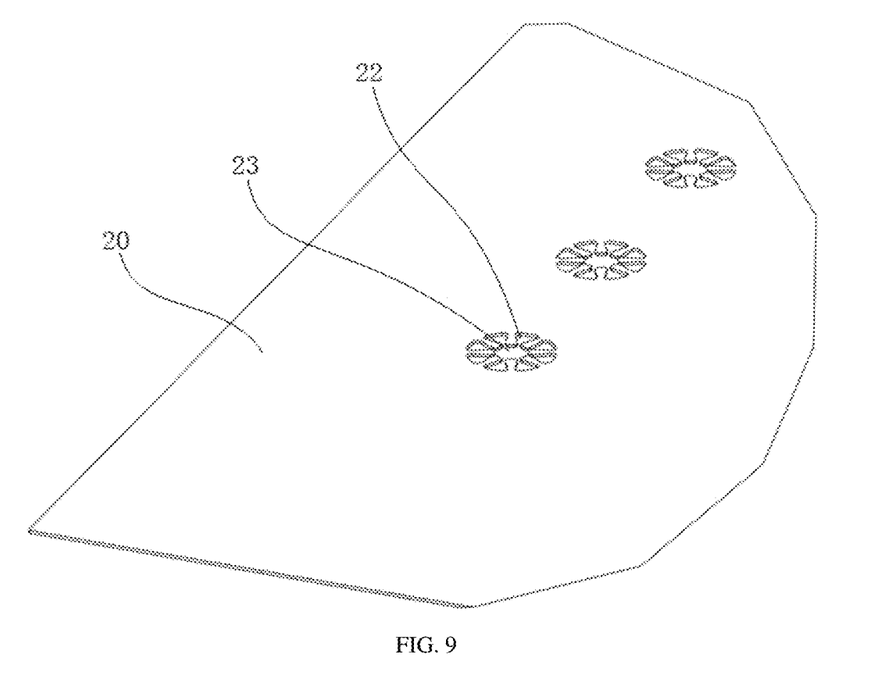
FIG. 9 is a schematic structural view of the soft needle tail of the present application.

In an embodiment, as shown in FIG. 7, FIG. 8 and FIG. 9, the second fixing member 12 is a plurality of pin structures 21 provided at intervals along the width direction of the hard needle 10 at the hard needle tail 19. The pin structure 21 is composed of two coaxial cylinders which are larger on the upper part and smaller on the lower part, a pin hole 23 is opened at the soft needle tail 20 corresponding to the pin structure 21, and a plurality of central symmetrical FIG. 22 are provided outwardly along the edge of the pin hole 23 on the soft needle tail 20, as shown in the figure in this embodiment, which can be a petal-like structure. The diameter of the upper cylinder of the pin structure 21 is larger than the diameter of the pin hole 23. When preparing the micro-needle body, after the soft needle 11 is grown on the hard needle 10, a pin hole 23 is opened on the soft needle tail 20, a central symmetrical FIG. 22 is graphically formed, and a pin structure 21 is grown at the pin hole 23. Since the diameter of the upper cylinder of the pin structure 21 is larger than the diameter of the pin hole 23, the upper cylinder will press part of the soft needle structure at the edge of the pin hole 23, thereby fixing the soft needle 11 and ensuring that no displacement occurs between the hard needle 10 and the soft needle 11. When the hard needle 10 drives the soft needle 11 to be implanted into the tissue together, by pulling the hard needle 10 downward, the upper cylinder of the pin structure 21 will exert a certain downward force on the soft needle 11, and the central symmetrical FIG. 22 on the soft needle 11 will bend and deform to a certain extent until the pin structure 21 is completely withdrawn. The hard needle 10 is pulled backward to withdraw the hook structure 16 on the hard needle 10, thereby making the hard needle 10 completely detached from the soft needle 11, and the hard needle 10 is pulled out, leaving the soft needle 11 in the tissue.

In this embodiment, the center point of central symmetrical FIG. 22 coincides with the center point of pin hole 23.

Figure 12:
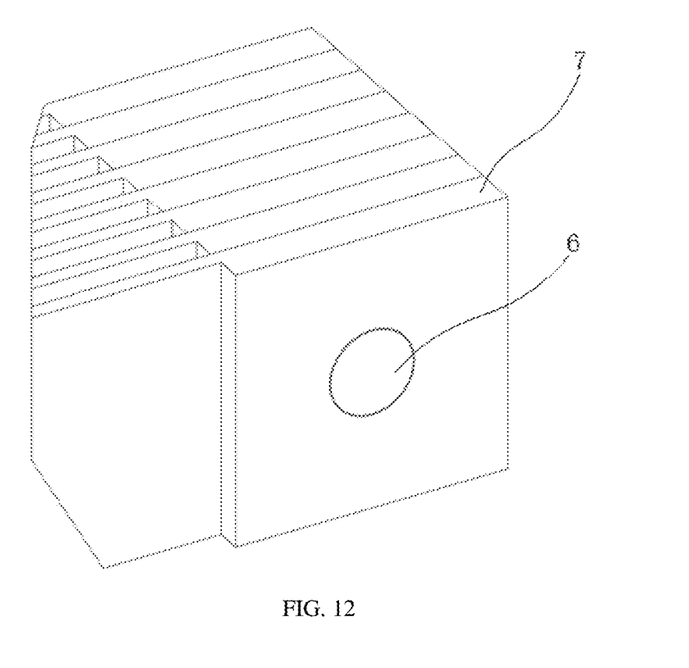
FIG. 12 is a schematic fixed structural view of a multi-layer integrated circuit chip of the present application.

As shown in FIG. 12, the two ends of the integrated circuit chip 7 are provided with connecting through holes. Multiple integrated circuit chips are assembled together by a binding structure. The binding structure passes through the connecting through holes on the same side. The binding structure can be but is not limited to steel needle 6. Multiple integrated circuit chips 7 are connected and fixed by punching and then passing through steel needle 6. Compared with the conventional through-silicon via (TSV) process, this connection method of the integrated circuit chip in this embodiment is simpler and more reliable to implement.

Figure 10:
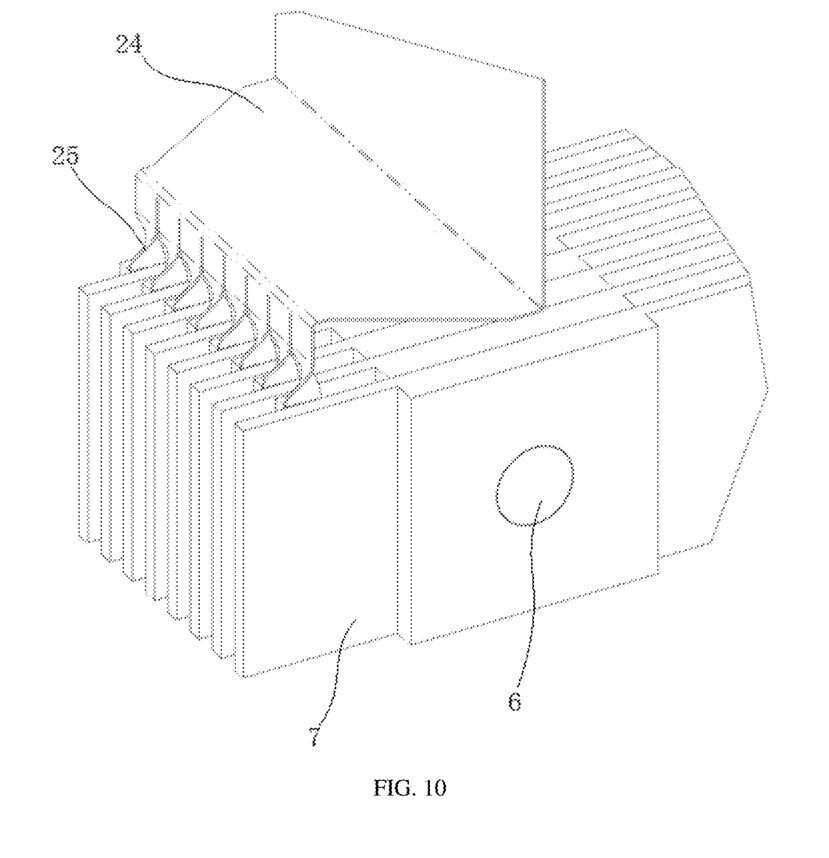
FIG. 10 is a schematic view of a reverse welding of a microstrip wire and an integrated circuit chip of the present application.

Regarding the connection between the microstrip wire 4 and the multiple integrated circuit chips 7, in this embodiment, as shown in FIG. 10, the microstrip wire 4 includes a bus 24 and a plurality of branch wires 25 connected to the bus 24, and each of the branch wires 25 is fixed to one end of each of the integrated circuit chips 7 by reverse welding. The microstrip wire 4 is directly reverse welded to each of the integrated circuit chips 7 to realize the local collection and stimulation of neural signals and ensure the stable and lossless transmission of signals.

The above embodiments are only examples of the present application and do not constitute a limitation on the scope of the present application. All designs that are the same or similar to the present application belong to the scope of the present application.

What is claimed is:

1. An area array micro-needle structure, comprising: a positioning partition plate and at least one micro-needle assembly, wherein the positioning partition plate comprises at least two comb structure members, and the comb structure member comprises a connecting plate and a plurality of racks formed on the connecting plate; and each of the racks is connected to the connecting plate in parallel at equal intervals, and the racks of the comb structure members are stacked to form the plurality of micro-needle holes distributed in an array for a body electrode of a micro-needle to pass through;

the micro-needle assembly comprises a micro-needle body, an integrated circuit chip provided at a tail of the micro-needle body, and a microstrip wire fixedly connected to one end of the integrated circuit chip to form an electrical connection; and the body electrode of each micro-needle body is configured to pass through the micro-needle hole of the positioning partition plate;

the micro-needle body comprises a hard needle and a soft needle, the hard needle is provided with a hard needle tail and at least one hard needle body electrode formed on the hard needle tail, and the soft needle is provided with a soft needle tail and at least one soft needle body electrode formed on the soft needle tail; the soft needle body electrode is correspondingly fixed with the hard needle body electrode through a first fixing member, and the soft needle tail is fixed with the hard needle tail through a second fixing member; and the integrated circuit chip is electrically connected to the soft needle tail through reverse welding; and the first fixing member is a plurality of hook structures provided at intervals along a length direction of the hard needle body electrode, and the hook structure is provided with a first part and a second part; one end of the second part is connected to the first part, and the other end of the second part is connected to a surface of the hard needle body electrode; an opening is provided on the soft needle body electrode at a position corresponding to the hook structure for the hook structure to pass through, and an unhook structure is provided on the opening for the hook structure to detach from the soft needle; and the second fixing member is a plurality of pin structures provided at intervals along a width direction of the hard needle tail.

2. The area array micro-needle structure according to claim 1, wherein a spacing between the racks of the comb structure members is larger than a width of the body electrode of the micro-needle or a thickness of the body electrode of the micro-needle.

3. The area array micro-needle structure according to claim 1, wherein the first part of the hook structure is parallel to the surface of the hard needle body electrode; and the soft needle body electrode is provided between the first part and the surface of the hard needle body electrode, and the second part is at a preset angle relative to the surface of the hard needle body electrode.

4. The area array micro-needle structure according to claim 1, wherein the unhook structure is an unhook portion extending from an edge of the opening into an inside of the opening, and a spacing between unhook portions is smaller than a width of the hook structure; and the unhook portions are symmetrically provided along an axis of the opening, and a gap is provided between a side edge of the unhook portion and a corresponding side edge of the opening.

5. The area array micro-needle structure according to claim 1, wherein the pin structure comprises two coaxial cylinders larger at upper part and smaller at lower part; and a pin hole is provided at the soft needle tail corresponding to the pin structure; a plurality of central symmetrical figures are provided outward along an edge of the pin hole on the soft needle tail, and a diameter of an upper cylinder of the pin structure is greater than a diameter of the pin hole.

6. The area array micro-needle structure according to claim 1, wherein connecting through holes are provided at both ends of the integrated circuit chip; and a plurality of integrated circuit chips are assembled together through a binding structure, and the binding structure is configured to pass through connecting through holes on a same side.

7. The area array micro-needle structure according to claim 1, wherein the microstrip wire comprises a bus and a plurality of branch wires connected with the bus, and each of the branch wires is correspondingly welded and fixed to one end of each of the integrated circuit chips through reverse welding.

* * * * *